(12) United States Patent
Aljuboori et al.

(10) Patent No.: US 12,299,806 B2
(45) Date of Patent: May 13, 2025

(54) METHOD AND APPARATUS FOR EVALUATING SURGICAL CORRIDORS IN THE SKULL

(71) Applicant: Wisconsin Alumni Research Foundation, Madison, WI (US)

(72) Inventors: Zaid Aljuboori, Madison, WI (US); Alan McMillan, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 197 days.

(21) Appl. No.: 17/809,403

(22) Filed: Jun. 28, 2022

(65) Prior Publication Data

US 2023/0419591 A1 Dec. 28, 2023

(51) Int. Cl.
| | |
|---|---|
| *G06T 15/08* | (2011.01) |
| *A61B 34/10* | (2016.01) |
| *G06T 15/10* | (2011.01) |
| *G06V 10/774* | (2022.01) |
| *G16H 20/40* | (2018.01) |
| *G16H 30/40* | (2018.01) |

(52) U.S. Cl.
CPC ............. *G06T 15/08* (2013.01); *A61B 34/10* (2016.02); *G06T 15/10* (2013.01); *G06V 10/774* (2022.01); *G16H 20/40* (2018.01); *G16H 30/40* (2018.01); *A61B 2034/105* (2016.02); *A61B 2034/107* (2016.02); *G06T 2210/41* (2013.01); *G06V 2201/03* (2022.01)

(58) Field of Classification Search
CPC ..... G06T 15/08; G06T 15/10; G06T 2210/41; A61B 34/10; A61B 2034/105; A61B 2034/107; A61B 2090/365; G06V 10/774; G06V 2201/03; G16H 20/40; G16H 30/40; G16H 40/60; G16H 50/20; G16H 50/70; G06N 20/00

See application file for complete search history.

(56) References Cited

U.S. PATENT DOCUMENTS

| | | | |
|---|---|---|---|
| 2015/0265236 A1* | 9/2015 | Garner | A61B 6/50 600/425 |
| 2015/0297309 A1* | 10/2015 | Bly | A61B 34/10 700/98 |
| 2017/0309069 A1* | 10/2017 | Thomas | A61B 34/20 |
| 2019/0327394 A1* | 10/2019 | Ramirez Luna | H04N 23/51 |
| 2019/0365475 A1* | 12/2019 | Krishnaswamy | A61B 17/3403 |
| 2019/0380780 A1* | 12/2019 | Sela | G09B 23/28 |
| 2020/0281670 A1* | 9/2020 | Moskowitz | A61B 34/30 |
| 2020/0297228 A1* | 9/2020 | Crawford | A61B 34/76 |
| 2021/0228143 A1* | 7/2021 | Yeh | G16H 50/70 |

(Continued)

OTHER PUBLICATIONS

Zaid Aljuboori et al.; "Morphometric Study of the Posterior Fossa: Identification of Practical Parameters for Tailored Selection of Surgical Routes to the Petroclival Region." Journal of Neurological Surgery Part B: Skull Base 83, No. 01 (2022): pp. 037-043; US (Year: 2022).*

(Continued)

Primary Examiner — Michael Le
(74) Attorney, Agent, or Firm — Boyle Fredrickson, SC

(57) ABSTRACT

A surgical planning tool evaluates a volumetric image of the skull to identify landmarks and define surgical corridors that can be compared and visualized for access to the skull for removal of tumors and the like.

18 Claims, 4 Drawing Sheets

(56) References Cited

U.S. PATENT DOCUMENTS

| | | | | |
|---|---|---|---|---|
| 2021/0244485 A1* | 8/2021 | Coiseur | ............... | A61B 34/20 |
| 2022/0354579 A1* | 11/2022 | Dyer | ................... | A61B 34/25 |
| 2022/0406460 A1* | 12/2022 | Golan | ................. | G16H 50/20 |
| 2022/0409281 A1* | 12/2022 | Gormley | .............. | A61B 34/25 |
| 2023/0149091 A1* | 5/2023 | Cohen-Gadol | ...... | G06T 15/08 |
| | | | | 606/1 |

OTHER PUBLICATIONS

Zaid Aljuboori et al.; "Morphometric Study of the Posterior Fossa: Identification of Practical Parameters for Tailored Selection of Surgical Routes to the Petroclival Region." Journal of Neurological Surgery Part B: Skull Base 83, No. 01 (2022): pp. 037-043; US.
Zaid Aljuboori et al.; "Predictors of the Size and Surgical Freedom of the Trans-Cribriform and Trans-Clival Corridors, a Radiographic Analysis." Journal of Neurological Surgery Part B: Skull Base (2021); pp. 1-7; Germany.

* cited by examiner

METHOD AND APPARATUS FOR EVALUATING SURGICAL CORRIDORS IN THE SKULL

STATEMENT REGARDING FEDERALLY SPONSORED RESEARCH OR DEVELOPMENT

This invention was made with government support under LM013151 awarded by the National Institutes of Health. The government has certain rights in the invention.

CROSS REFERENCE TO RELATED APPLICATION

BACKGROUND OF THE INVENTION

The present invention relates to surgery of the human skull and in particular to a tool to assess surgical routes for difficult skull base lesions.

Lesions inside the skull, and at its base, are challenging to treat, requiring the selection of a surgical corridor through the skull to the lesion. Multiple surgical corridors (e.g., transclival, anterior petrous, and translabyrinthine) make use of pathways that remove portions of the bony skull base selected to minimize brain retraction and injury to critical neurovascular structures.

The size and surgical freedom of these surgical corridors varies and is determined by the bony anatomy of the patient. Despite the importance of the corridor dimensions, currently, the choice of a surgical corridor depends largely on surgeon preference with limited emphasis on bony anatomy. In part, this may be a natural result of the difficulty of accurately assessing and comparing corridor dimensions in the complex anatomy of the petroclival region.

SUMMARY OF THE INVENTION

The present invention provides a tool for quantitatively assessing surgical corridors in the human skull. Consistent and reliable identification of critical bony anatomy defining the corridor is provided by a trained machine learning system using volumetric skull data. This identification provides a foundation for a quantitative geometric definition of the constraining features of the corridor, including corridor area and surgical freedom, and allows a direct comparison of different corridors for surgical planning.

More specifically, in one embodiment, the invention provides and apparatus for evaluating surgical corridors through the skull having an input for receiving volumetric image information describing a patient's skull and a machine learning engine trained with skull volume data for multiple individuals linked to identified anatomical regions of the skull for at least one predetermined surgical corridor. The machine learning engine operates to receive the volumetric image information and to identify patient anatomical regions for the patient's skull. A geometric processor receives the patient anatomical regions to generate a volume conforming to the at least one of the predetermined surgical corridors and output providing a description of the volume adapted to provide guidance to a healthcare professional.

It is thus a feature of at least one embodiment of the invention to permit rapid and objective comparison of surgical corridors for improved surgical planning.

The output may indicate at least one of a size and surgical freedom of the volume.

It is thus a feature of at least one embodiment of the invention to develop simple quantitative metrics for surgical corridors amenable to clear comparison.

The geometric processor may generate the volume registered to the volumetric image information describing the patient's skull and the output may provide a visual representation of the corridor.

It is thus a feature of at least one embodiment of the invention to provide a visual representation of the corridor, for example, including additional interfering structures like nerves and blood vessels.

The apparatus may provide an input for receiving volumetric information describing a tumor within the skull and the output visual representation may provide a projection of the tumor and volume along an adjustable line-of-sight.

It is thus an object of at least one embodiment of the invention to assist in evaluation of surgical corridors and in surgical planning through a visual simulation representing the surgical corridor.

The machine learning engine may be trained with skull volume data for multiple individuals linked to identified anatomical regions for more than one predetermined surgical corridor, and the geometric processor may generate volumes for each of the more than one predetermined surgical corridors, and the output may provide a chart comparing those volumes.

It is thus a feature of at least one embodiment of the invention to rapidly assess multiple surgical corridors and provide guidance to the surgeon for selecting among these multiple choices.

The machine learning engine maybe trained with skull volume data for multiple individuals linked to at least two identified anatomical regions of the skull displaced along a predetermined surgical corridor and defining a corridor entrance and exit, the machine learning engine operating to receive the volumetric image information and to identify at least two patient anatomical regions for the patient, and wherein the geometric processor receives the at least two identified patient anatomical regions from the machine learning engine to generate a volume conforming to both of the at least two identified patient anatomical regions.

It is thus a feature of at least one embodiment of the invention to permit assessment of surgical corridors, for example, that are constrained by more than one opening in the skull, for example, an opening in the petroclival region and the bony nasal opening used with endonasal access.

These particular objects and advantages may apply to only some embodiments falling within the claims and thus do not define the scope of the invention.

Figure 4:
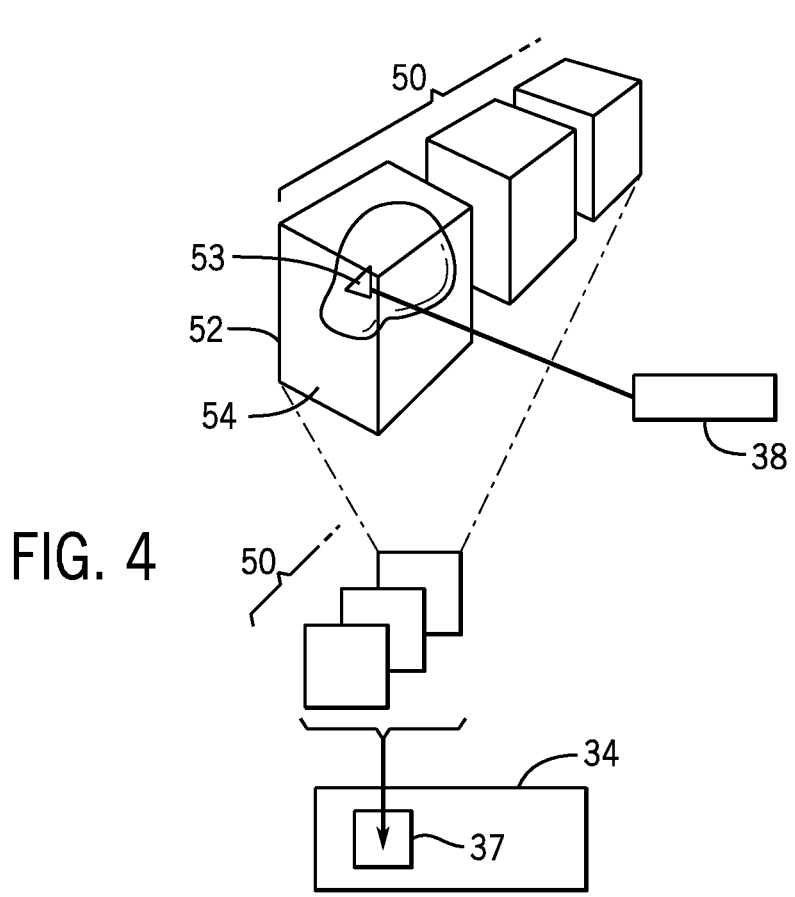
FIG. 4 is a process representation of the training of a machine learning system for the different corridors of FIG.
Figure 5:
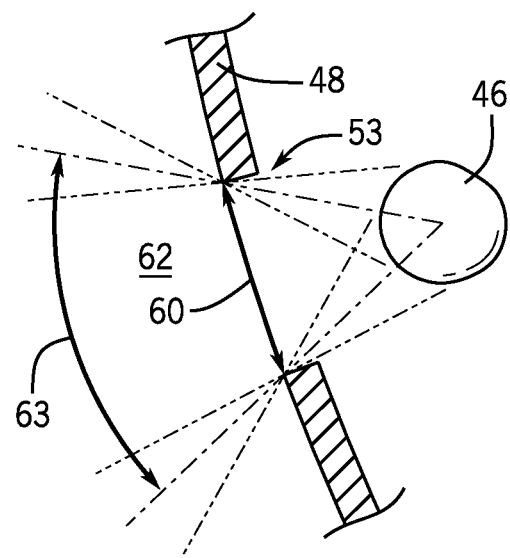
Figure 6:
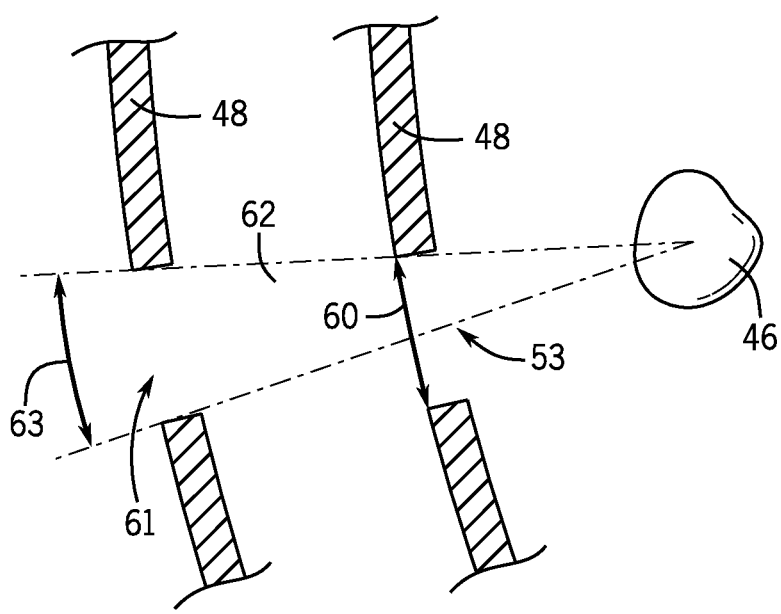
Figure 7:
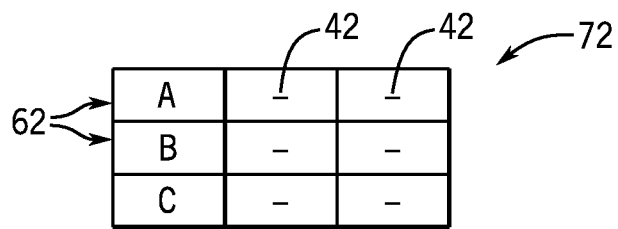
Figure 8:
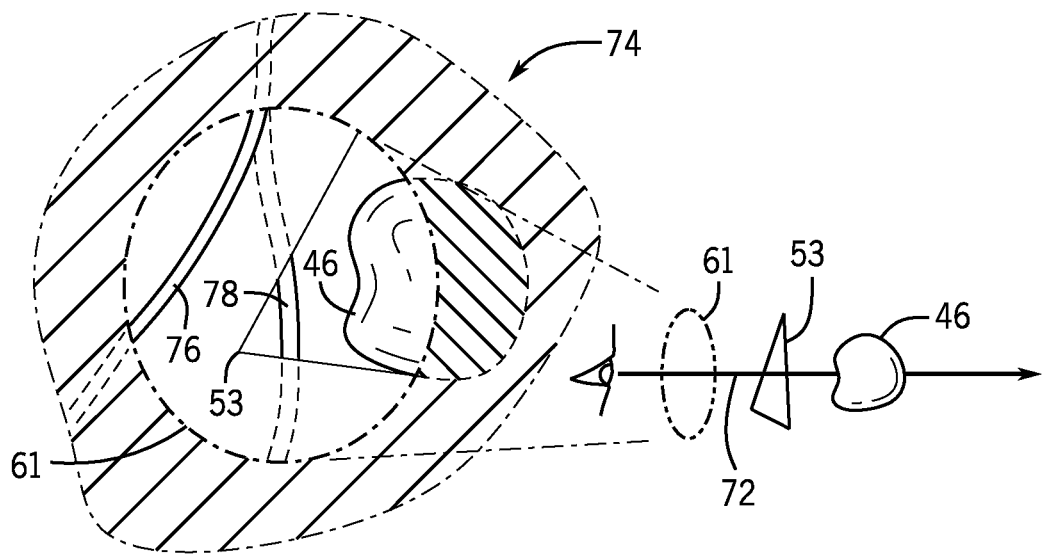

3 using a training set that may be manually segmented to identify anatomical regions for each corridor;

FIG. 5 is a representation of a geometric calculation of surgical freedom and corridor area making use of anatomical regions identified by the machine learning system of FIG. 4;

FIG. 6 is a figure similar to that of FIG. 5 showing the geometric calculation in an endoscopic endonasal approach;

FIG. 7 is a representation of an output chart allowing comparison of surgical corridors; and FIG. 8 is a representation of an output image providing projection of corridor volume on tumor volume to allow a visual and intuitive understanding of the corridor dimension limitations.

DETAILED DESCRIPTION OF THE PREFERRED EMBODIMENT

Figure 1:
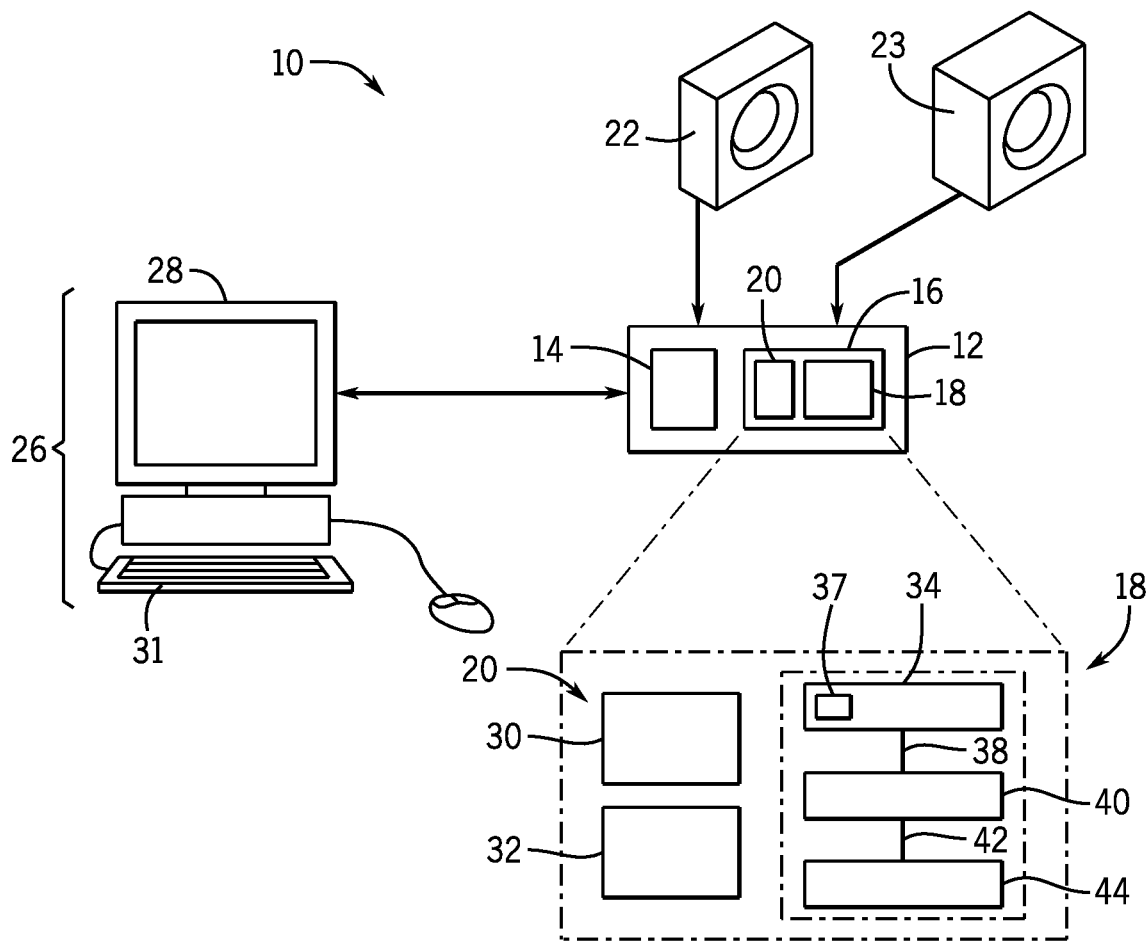
FIG. 1 is a simplified block diagram of the components of the present invention as may be implemented in an electronic computer receiving volumetric data from one or more medical imaging machines.

Referring now to FIG. 1, a surgical planning tool 10 according to one embodiment of the invention may provide an electronic computer 12 having one or more processors 14 communicating with computer memory 16. The computer memory 16 may hold a stored program 18 as well as data 20, for example, received from a computed tomography (CT) machine 22 and/or an magnetic resonance imaging (MRI) machine 23 or other imaging modalities, as well as machine learning weights and other data to be described below. The electronic computer 12 may communicate with a user terminal 26 having a graphic display screen 28 and user input device 31, for example, a keyboard, for providing inputs to the electronic computer 12 for execution of the program 18 and for receiving and displaying outputs from the program 18 when the program 18 is executed as will be described.

Figure 2:
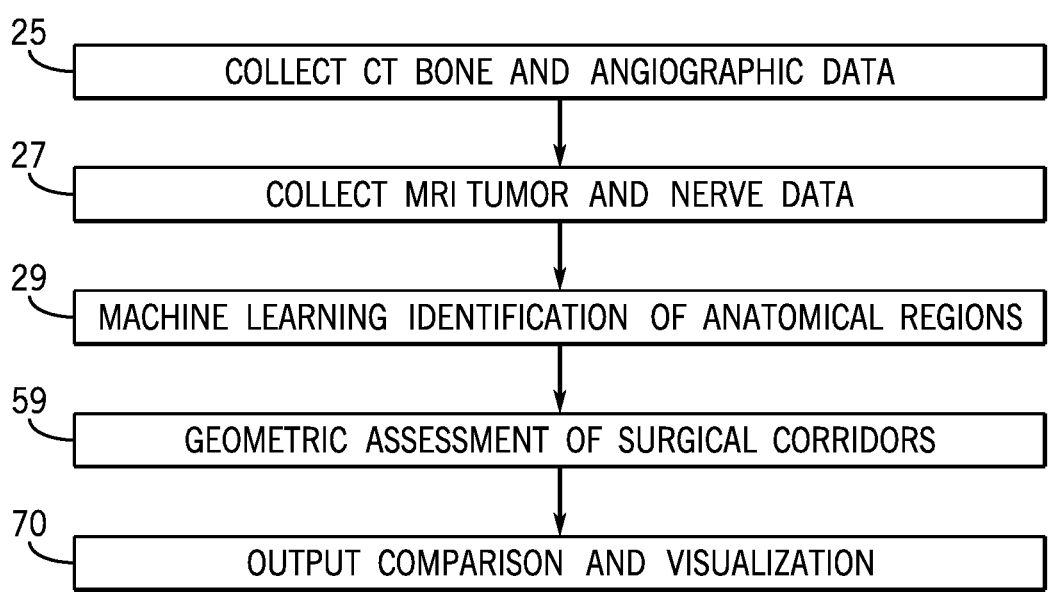
FIG. 2 is a flowchart of processes executed on the electronic computer of FIG. 1 including a machine identification of anatomical regions and the geometric determination of surgical corridor parameters.

Referring now also to FIG. 2, during operation of the surgical planning tool 10, the program 18 may receive data 20 from associated medical imaging machines including a CT machine 22 which may provide a volumetric bone image 30 of a patient's skull (segmented from soft-tissue according to techniques known in the art) as indicated by process block 25. As is generally understood in the art, a volumetric image provides a set of voxels in three dimensions describing values of tissue of the patient at those corresponding three-dimensional locations. More generally, some or all of this data can be collected in a single step, for example, on a single imaging machine or combination machine or the like, to provide contemporaneous data that is inherently registered.

Per process block 27, one or more volumetric soft-tissue images 32 registered to the volumetric bone image 30 from the CT machine 22 may also be acquired including: an image of a tumor within the patient's skull as well as images of local blood vessels (e.g., the internal cardioid artery) and cranial nerves, for example, using MR or CT angiography and MRI neurography or the like. The soft-tissue images 32 may be manually or automatically segmented to describe the tumor, blood vessels, and nerves isolated from other tissue and each other.

As indicated by process block 29, the volumetric bone image 30 of the skull may then be provided to a machine learning engine 34 programmed with a set of weights 37 to identify and output the locations of anatomical boney landmarks 38, for example, with a mask identifying collections of voxels of the volumetric bone image 30 and related to particular surgical corridors.

Referring now to FIG. 4, the weights 37 of the machine learning engine 34 may be developed from a training set 50 from multiple volumetric bone images 52 from a set of patients. In one embodiment, these bone images 52 may be acquired from patients between 18 years and 75 years of age selected to exclude those with radiographic evidence of trauma neoplasm inflammation infection, previous surgery, or congenital malformations of the skull base. These bone images 52 may be high-resolution (512×512×1 mm slice thickness) CT scans.

Manual segmentation of each image 52 may be performed by an expert reader, for example, using the software tool ITKSnap, an open source program developed at the University of Pennsylvania and University of Utah to identify a set of bony anatomical references for each image 52 for each of a selected set of surgical corridors.

Figure 3:
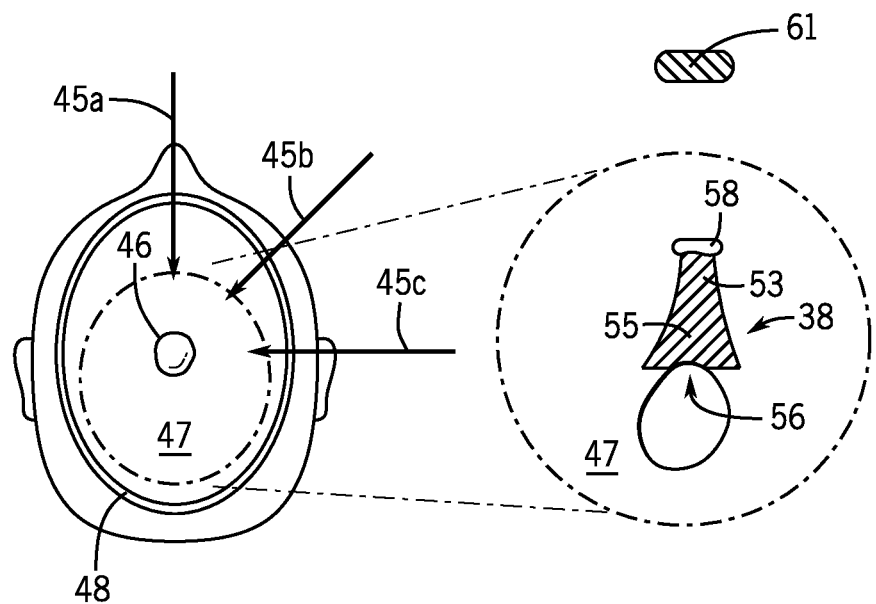
FIG. 3 is a top plan view of a patient's head in phantom showing a tumor and multiple example surgical corridor options and showing in an expanded view the petroclival region of the skull base and relevant anatomy for transclival access.

Referring now to FIG. 3, in one nonlimiting embodiment, three different corridors 45 to a skull base tumor 46 may be considered including: a transclival corridor 45a passing into the petroclival region 47 of the skull 48 through the nasal cavity, an anterior petrous corridor 45b entering the petroclival region 47 at an angle to the sagittal plane from an anterior side of the head, and a translabyrinthine corridor 45c entering laterally from a side of the head in the direction generally parallel to the coronal plane. For analyzing these corridors, the following bony anatomical references 38 will be identified for each image 52 by the expert reader.

TABLE I

| Corridor | Anatomical Landmarks |
|---|---|
| Anterior petrous corridor | petroclival fissure, internal acoustic meatus, and apetrous internal carotid artery |
| Translabyrinthine corridor | external acoustic meatus, internal acoustic meatus, petrous ridge, and lateral border of the mastoid process |
| Transclival corridor | the area of the clivus from the anterior foramen magnum to the floor of the sella; the area of the bony nasal opening |

Each of the images 52 is then tagged with a set of masks or geometric descriptions of the identified anatomical landmarks 38 to provide an augmented teaching volume image 54. For example, and referring to FIG. 5, for the transclival corridor, a first anatomical landmark 38 may be the area of the clivus 55 from the anterior of the foramen magnum 56 to the floor of the sella 58 and a second anatomical landmark 38 will be the opening the bony nasal opening 61. For the transclival corridor, an opening 53 is formed by removing this area of the clivus 55.

The training set 50 of the augmented teaching volume images 54 is then provided to a deep convolutional neural network, for example, implemented using the MONAI framework, an open-source project originated by NVIDIA of Santa Clara, California, and King's College, London, utilizing deep learning framework PyTorch, an open source project originally developed by Meta Platforms, Inc, and 3D Unet with integrated transformers, named the UNETR described in Hatamizadeh, A., Tang, Y., Nath, V., Yang, D., Myronenko, A., Landman, B., Roth, H. and Xu, D., 2021. Unetr: Transformers for 3d medical image segmentation, arXiv preprint arXiv:2103.10504. The segmentation may, for example, use a patch-based 3D approach, where cubic patches of 96×96×96 pixels are fed into the model from the high-resolution CT input and segmentation masks. Training parameters may use the AdamW optimizer with a learning rate of 0.0001 using the Dice coefficient loss across 25,000 training iterations. UNETR model hyperparameters may be manually modified on an as-needed basis, starting with the default settings. Model weights may be randomly initiated for each training run. The data may be split into a training set of N=400 subjects and a validation/testing set of N=100 subjects. Five-fold cross validation may be used to ensure each subject is included in the testing set at least once. For each evaluation fold, 25% of the testing dataset may be manually verified by an expert reader to visually confirm adequate segmentation of each of the three landmarks.

This training set 50 is used to train the machine learning engine 34 to automatically provide the segmentation for identification of the anatomical landmarks 38 directly from the volumetric bone image 30. The result of the training is to provide the set of weights 37 such that the machine learning engine 34 may receive the volumetric bone image 30 from a novel patient and provide identified anatomical landmarks 38 per Table I above.

Referring now to FIGS. 1, 2, and 5, after analysis of the volumetric bone image 30 by the machine learning engine 34, the identified anatomical landmarks 38 are provided to a geometric calculator 40 to determine corridor dimensions 42 characterizing each of a set of corridors (for example, listed in Table I) as constrained by the anatomical landmarks 38 per process block 59 of FIG. 2. These corridor dimensions 42 may be in the form of a corridor opening size and a corridor degree of surgical freedom which may be calculated geometrically, for example, using standard computer programming techniques.

When only a single opening in the skull 48 is required, for example, with the corridors 45b and 45c shown in FIG. 3, a surgical corridor 62 may be defined by the area 60 defined by the anatomical landmarks 38 (represented by a one-dimensional arrow in FIG. 5) and typically representing an opening cut through the skull 48, where the anatomical landmarks 38 are selected to indicate portions of the skull amenable to removal with minimal complications. In addition, the surgical corridor 62 surgical freedom may be defined by an angle 63 subtended by a set of rays or lines extending from the surgical target (e.g., the tumor 46) to a location outside of the skull accessible by the surgeon. These lines may originate either from the extreme edges of the tumor or from its center point as may be selected. Separate angles of surgical freedom can be computed in an anterior-posterior direction and a lateral direction parallel to the transverse plane, or an average angle subtended by a cone having an irregular basis defined by the area 60 may be used. When an image or other definition of the tumor 46 is not available, a proxy target object may be used having an average tumor size and average separation from the inner surface of the skull 48.

Referring now to FIG. 6, in the case of the transclival corridor which may employ an endonasal endoscope during surgery, the area 60 may be defined identically by the anatomical landmark 38 (in this case the area of the clivus 55 described above) but the angle 63 of surgical freedom may be constrained by combination of the opening 53 and bony nasal opening 61 and their relative spacing along the corridor as indicated.

Alternative measures of these quantities can also be developed and consistently applied for the purposes of comparison of surgical corridors.

Referring now to FIGS. 2 and 6, as indicated by process block 70 of FIG. 2, the measures of the different surgical corridors are then provided to an output processor 44 which may output data on the graphic display screen 28 allowing for a quantitative comparison of the different surgical corridors in a table 73, for example, having rows indicating the different corridors and columns providing the quantitative corridor dimensions 42 described above, for example, area and surgical freedom. In this way the surgeon can readily assess different surgical corridors 62.

Referring now also to FIG. 8, in addition, the surgical corridor 62 may be painted on the volumetric bone image 30, for example, using different transparent shadings for each different corridors, registered to the volumetric bone image 30 which may be viewed at different angles. The rotation of the volumetric bone image 30 and the surgical corridor 62 changes a line-of-sight 72 and thus a projection 74 of the various corridors 62 and anatomical landmarks 38 (which may also be shaded in the areas 60 and opening 61), allowing the surgeon to view down the corridor 62 in a perspective simulating that of surgery. This projection may also show (by shading) 3-D renderings of nerves 76 and arteries 78 obtained from the volumetric soft-tissue images 32 so that other obstructions can be considered in evaluating the corridor 62. By changing the line-of-sight 72 various corridors 62 can be visually compared.

While the nerves 76 in arteries 78 are described with respect to visual assessment above, it will be understood generally structures of the nerves 76 and arteries 78 may also be treated as anatomical landmarks 38 to define the surgical corridor 62 in consideration of the need to avoid certain nerves and arteries.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

Machine learning as used herein refers to computational systems that our program through the use of teaching sets and experience with data using the principles of artificial intelligence. Generally such machine learning systems will include a set of weight values derived from training and providing weights of inputs through interconnected neurons or the like forming an artificial neural network.

Electronic computer 12 as described above can be understood to include one or more standard computer processors or dedicated circuitry such as FPGAs, ASICS or the like that can communicate in a stand-alone and/or a distributed environment(s), and can thus be configured to communicate via wired or wireless communications with other processors, where such one or more processors can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network. Generally each of the machine learning engine 34 and computation are 40 may be implemented as separate dedicated devices. It will also be understood that the geometric processor may be implemented by standard computer programming or may use a similar machine learning system using a training set in which surgical corridors are identified by experts.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What we claim is:

1. An apparatus for evaluating surgical corridors through the skull comprising:
   an input for receiving volumetric image information describing a patient's skull;
   a machine learning engine trained with skull volume data describing skull anatomy for multiple individuals linked to a set of predetermined anatomical regions of the skull for at least one surgical corridor through that individual's skull, the machine learning engine operating to receive the volumetric image information and to identify patient anatomical regions of predetermined surgical corridors through the skull specific to the patient's skull;
   a geometric processor receiving the patient anatomical regions of predetermined surgical corridors through the skull specific to the patient's skull to generate a volume conforming to the at least one of the predetermined surgical corridors through the skull specific to the patient's skull; and
   an output selected from the group consisting of quantitative corridor dimensions of the predetermined surgical corridors through the skull specific to the patient's skull and a graphic representation of the volume.

2. The apparatus of claim 1 wherein the output indicates at least one of a size and surgical freedom of the volume.

3. The apparatus of claim 1 wherein the geometric processor generates the volume registered to the volumetric image information describing the patient's skull.

4. The apparatus of claim 3 wherein the output provides a visual representation of the corridor.

5. The apparatus of claim 4 further providing an input for receiving volumetric information describing a tumor within the skull and wherein the output visual representation provides a projection of the tumor and volume along an adjustable line-of-sight.

6. The apparatus of claim 1 wherein the machine learning engine is trained with skull volume data for multiple individuals linked to identified anatomical regions for more than one predetermined surgical corridor and wherein the geometric processor generates volumes for each of the more than one predetermined surgical corridors and the output provides a chart comparing those volumes.

7. The apparatus of claim 6 wherein the chart indicates at least one of volume and surgical freedom of the corridor for each of the compared volumes.

8. The apparatus of claim 1 wherein the surgical corridor is selected from the group consisting of transclival, anterior petrous, and translabyrinthine corridors through the skull.

9. The apparatus of claim 1 wherein the anatomical regions are selected from the group consisting of: a petroclival fissure, an internal acoustic meatus, a petrous internal carotid artery, an external acoustic meatus, a semicircular canal, a petrous ridge, a lateral border of the mastoid process, and an area of the clivus from the anterior foramen magnum to the floor of the sella.

10. The apparatus of claim 1 wherein the machine learning engine is trained with skull volume data for multiple individuals linked to at least two identified anatomical regions of the skull displaced along a predetermined surgical corridor and defining a corridor entrance and exit, the machine learning engine operating to receive the volumetric image information and to identify at least two patient anatomical regions for the patient, and wherein the geometric processor receives the at least two identified patient anatomical regions from the machine learning engine to generate a volume conforming to both of the at least two identified patient anatomical regions.

11. The apparatus of claim 10 wherein one of the patient anatomical regions is a bony nasal opening.

12. A method for evaluating surgical corridors through the skull comprising:
   (a) acquiring volumetric image information describing a patient's skull;
   (b) providing the volumetric image to a machine learning engine trained with skull volume data describing skull anatomy for multiple individuals linked to a set of predetermined anatomical regions of the skull for at least one surgical corridor through that individual's skull, the machine learning engine operating to receive the volumetric image information and to identify patient anatomical regions of predetermined surgical corridors through the skull specific to the patient's skull;
   (c) applying the identified patient anatomical regions of the skull to a geometric processor to generate a volume conforming to the at least one of the predetermined surgical corridors through the skull specific to this patient's skull; and
   (d) generate and output description of the volume selected from the group consisting of quantitative corridor dimensions of the predetermined surgical corridors through the skull specific to the patient's skull and a graphic representation of the volume.

13. The method of claim 12 wherein the output indicates at least one of volume and surgical freedom.

14. The method of claim 13 wherein the geometric processor generates the volume registered to the volumetric image information describing the patient's skull and wherein the output provides a visual representation of the corridor.

15. The method of claim 14 further including the step of acquiring volumetric information describing a tumor within the skull and wherein the output visual representation provides a projection of the tumor and volume along an adjustable line-of-sight.

16. The method of claim 12 wherein the machine learning engine is trained with skull volume data for multiple individuals linked to identified anatomical regions for more than one predetermined surgical corridor and including the step of using the geometric processor to generate volumes for each of the more than one predetermined surgical corridors wherein the output provides a chart comparing those volumes.

17. The method of claim 16 wherein the chart indicates at least one of volume and surgical freedom of the corridor for each of the compared volumes.

18. The method of claim 12 wherein the machine learning engine is trained with skull volume data for multiple individuals linked to at least two identified anatomical regions of the skull displaced along a predetermined surgical corridor and defining a corridor entrance and exit, including the step of providing the machine learning engine with the volumetric image information and identifying at least two patient anatomical regions for the patient, including the step of providing the geometric processor with the at least two identified patient anatomical regions from the machine learning engine to generate a volume conforming to both of the at least two identified patient anatomical regions.

* * * * *